United States Patent [19]

Reineke

[11] 4,125,555
[45] * Nov. 14, 1978

[54] TRIFLUOROMETHANESULFONATES

[75] Inventor: Charles E. Reineke, Midland, Mich.

[73] Assignee: The Dow Chemical Company, Midland, Mich.

[*] Notice: The portion of the term of this patent subsequent to Jul. 26, 1994, has been disclaimed.

[21] Appl. No.: 799,802

[22] Filed: May 23, 1977

Related U.S. Application Data

[63] Continuation-in-part of Ser. No. 688,862, May 21, 1976, Pat. No. 4,038,245.

[51] Int. Cl.² .................. C07C 143/68; C08K 5/41; A61K 31/255; A01N 9/14
[52] U.S. Cl. .................. 260/456 F; 71/103; 260/45.75; 260/DIG. 24; 424/303; 526/3
[58] Field of Search .................. 260/456 F, 45.7 SF

[56] References Cited

U.S. PATENT DOCUMENTS

| | | | |
|---|---|---|---|
| 3,419,595 | 12/1968 | Hansen | 260/456 F |
| 4,038,245 | 7/1977 | Reineke | 526/3 |

OTHER PUBLICATIONS

Kobayashi et al., Bul. Chem. Soc. of Japan, 47-2699 (1974).

Primary Examiner—Nicky Chan
Attorney, Agent, or Firm—James B. Guffey

[57] ABSTRACT

Novel esters of the formula:

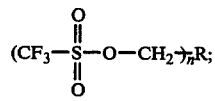

promote char formation in polymer compositions containing a monovinylidene aromatic monomer, such as styrene, and an ethylenically unsaturated carboxylic anhydride, such as maleic anhydride. In such esters, R is an n-valent tertiary hydrocarbyl radical, an n-valent tertiary chlorohydrocarbyl radical, an n-valent tertiary hydrocarbyl radical containing at least one chain linkage of oxygen or an inertly substituted n-valent tertiary hydrocarbyl radical containing at least one bromine atom.

8 Claims, No Drawings

TRIFLUOROMETHANESULFONATES

CROSS-REFERENCE TO RELATED APPLICATION

This application is a continuation in part of my co-pending application, Ser. No. 688,862 (now U.S. Pat. No. 4,038,245), filed May 21, 1976, the disclosure of which is hereby incorporated by reference.

BACKGROUND OF THE INVENTION

This invention relates to trifluoromethanesulfonate esters.

Certain esters of trifluoromethanesulfonic acid have been reported in the literature. See, for example, the esters listed in Table A.

TABLE A

| Trifluoromethanesulfonate Ester | References |
|---|---|
| Methyl | K |
| Ethyl | K, L, M, N |
| n-Propyl | A, B |
| Isopropyl | B, C |
| 1,2,3-Propanetriyl | C |
| 1,4-Butanediyl | C |
| n-Pentyl | B, C |
| Allyl | B, C |
| Propargyl | C |
| 2-(2-Fluoro-2,2-dinitroethoxy)ethyl | C |
| 2-Fluoro-2,2-dinitroethyl | C |
| n-Hexyl | B |
| n-Decyl | B |
| Benzyl | D |
| Phenyl ethyl | E |
| Aryl and substituted aryl | F, O |
| Various vinyl esters | G, H, I |
| Various esters of normally unreactive mono- and polycyclic alcohols | J |
| Various fluorinated straight chain alkyls | P |
| 3-Ethoxy-2,2-bis(chloromethyl)propyl | N |

A: Dafforn et al., Tetrahedron Letters, No. 36, 3159–3162 (1970).
B: Beard et al., J. Org. Chem., Vol. 39, No. 26, 3875–7, (1974).
C: Beard et al., J. Org. Chem., Vol. 38, No. 21, 3673–7 (1973).
D: Lemieux et al., Carbohydrate Research, 35, pp. C4–C6 (1974).
E: Lee et al., Can. J. Chem., Vol. 52, No. 23, 3955–3959, (1974)
F: Yagupol'skie, et al., Zh. Org. Khim., Vol. 7, No. 5, 996–1001 (1971). Abstracted at Chem. Abstracts, Vol. 75, page 324 (1971).
G: Hanack, Accounts of Chemical Research, Vol. 3, No. 7, 209–216 (1970)
H: Stang et al., J. Am. Chem. Soc., 91:16, 4600–4601 (1969)
I: Jones et al., J. Am. Chem. Soc., 91:15, 4314–4315 (1969)
J: Su et al., J. Am. Chem. Soc., 91:19, 5386–5388 (1969)
K: Gramstad et al., J. Chem. Soc., 4069 (1957)
L: Kobayashi et al., Bul. Chem. Soc. of Japan, Vol. 46, 3214–3220 (1973)
M: Kobayashi et al., Macromolecules, Vol. 4, 415–420 (1974)
N: Kobayashi et al., Bul. Chem. Soc. of Japan, Vol. 47(II), 2699–2701 (1974)
O: U. S. Pat. No. 3,346,612
Hansen, J. Org. Chem., Vol. 30, 3422–4324 (1965)

Certain of the aforementioned esters have been found useful for certain specific purposes. For example, the aryl esters are reported to be useful as low flammability lubricants and hydraulic fluids and, in certain instances, as intermediates for dyestuffs, pharmaceuticals and photographic chemicals. Others (e.g., n-alkyl and fluorinated n-alkyl) by virtue of extreme reactivity have been found to have utility as alkylating agents and as ring-opening polymerization initiators for certain monomers. Other of the aforementioned esters have been found to have no practical utility.

My copending application Ser. No. 688,862 discloses that certain trifluoromethanesulfonate esters are useful as char-forming agents in specified polymer compositions. Certain of the specified char-forming esters are new chemical compounds. Such new compounds constitute the subject matter of this invention.

SUMMARY OF THE INVENTION

This invention is a novel trifluoromethanesulfonate of the formula:

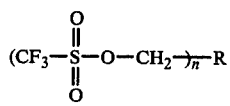

$$(CF_3-S(=O)_2-O-CH_2)_n-R$$

wherein $n$ is a positive integer and R is an n-valent tertiary hydrocarbyl radical, as n-valent tertiary chlorohydrocarbyl radical, an n-valent tertiary hydrocarbyl radical containing at least one chain linkage of oxygen or an inertly substituted n-valent tertiary hydrocarbyl radical containing at least one bromine atom.

Such trifluoromethanesulfonate esters (hereinafter also referred to as "triflate esters") are useful as char-forming agents in certain polymer compositions as disclosed in Ser. No. 688,862. Certain of such triflate esters are also useful as herbicides and/or as antimicrobial agents and/or as insecticides.

DETAILED DESCRIPTION OF THE INVENTION

The triflate esters comprise a number of triflate ester moieties of the formula, $CF_3-SO_3-CH_2-$, corresponding to $n$ wherein $n$ is a positive integer. Preferably $n$ is from 1 to about 9; more preferably $n$ is from 1 to about 6; and most preferably $n$ is 1 or 2.

In the triflate esters, R is an n-valent tertiary hydrocarbyl radical, an n-valent tertiary chlorohydrocarbyl radical, an n-valent tertiary hydrocarbyl radical containing at least one chain linkage of oxygen or an inertly substituted n-valent tertiary hydrocarbyl radical containing at least one bromine atom. Preferably such radical contains from 1 to about 9 valency carbon atoms, more preferably from 1 to about 3 valency carbon atoms, and most preferably 1 valency carbon atom. As used herein, valency carbon atom means a carbon atom, within the radical R, which is bonded to one or more triflate ester moieties, as previously defined. As used herein, n-valent means that the hydrocarbyl radical is bonded to $n$ triflate ester moieties. The term "hydrocarbyl" means a hydrocarbon radical having the indicated valency.

The term "tertiary" means that each valency carbon atom in the hydrocarbyl radical is bonded to 4 carbon atoms including the carbon atom in each triflate ester moiety to which the valency carbon atom is bonded. Accordingly, the valency carbon atom will be bonded to between zero and 3 carbon atoms which are not contained within a triflate ester moiety. Thus the hydrocarbyl radical is "tertiary" in the sense that, as to a given triflate ester moiety, it is tertiary (i.e., bonded to 3 additional carbon atoms). Subject to the requirement that each valency carbon atom is bonded to a total of 4 carbon atoms, the tertiary hydrocarbyl radical can be an aliphatic, alicyclic or aromatic radical, for example, an alkyl radical, an alkenyl radical, a cycloalkyl radical, a cycloalkenyl radical, an aralkyl radical, an aralkenyl radical, an arcycloalkyl radical, an arcycloalkenyl radical, and the like.

The term "inertly substituted" means that the hydrocarbyl radical contains substituents, such as halogen atoms, and/or chain linkages, such as oxygen or sulfur atoms, which do not interfere with the preparation of the triflate ester. Thus, for example, inertly substituted tertiary hydrocarbyl radicals include halogenated tertiary hydrocarbyl radicals such as halo-t-alkyl, haloaryl-t-alkyl and similar halogenated tertiary hydrocarbyls wherein tertiary hydrocarbyl is as defined and exemplified hereinbefore; hydrocarbyloxy-t-hydrocarbyl radicals such as, alkoxy-t-alkyl, haloaryloxy-t-alkyl, aryloxy-t-alkenyl and similar radicals wherein tertiary hydrocarbyl is as defined hereinbefore and hydrocarbyl is alkyl, haloalkyl, aryl, haloaryl, aralkyl, alkenyl, aralkenyl, cycloalkyl, cycloalkenyl, arcycloalkyl, arcycloalkenyl, alkaryl, alkenylaryl, cycloalkylaryl, cycloalkenylaryl and similar monovalent hydrocarbyl and halogenated hydrocarbyl radicals; and hydrocarbylthio-t-hydrocarbyl radicals, such as alkylthio-t-alkyl, haloarylthio-t-alkyl, cycloalkylthio-t-alkyl, alkarylthio-t-cycloalkenyl, and similar hydrocarbyl and halogenated hydrocarbyl radicals wherein tertiary hydrocarbyl and hydrocarbyl are as defined and exemplified hereinbefore.

While the total carbon content of the radical R is not critical, it will generally contain from 1 to about 40, preferably from 1 to about 24, and most preferably from 1 to about 18 carbon atoms.

Naturally since R is "tertiary" as to a single triflate ester moiety, the minimum possible carbon content of R will depend upon the number of triflate ester moieties to which R is bonded and upon the number of valency carbon atoms contained by R. Thus, for example, when R contains one valency carbon atom, the minimum carbon content of R is (5-n) wherein valency carbon atom and $n$ are as hereinbefore defined. Similarly when R contains 2 valency carbon atoms, the minimum carbon content of R is (8-n). In a like manner when R contains more than 2 valency carbon atoms, the minimum carbon content of R will be that which is required, for a given value of $n$, for each valency carbon to be bonded to a total of 4 carbon atoms.

Examples of the aforementioned triflate esters include 2,2-dimethylpropyl trifluoromethanesulfonate; 2,2-dimethyl-1,3-propanediyl trifluoromethanesulfonate; triflate esters of dimers, trimers, etc. of polyols such as pentaerythritol, trimethylol ethane, trimethylol propane, neopentyl glycol, etc.; 2,2-bis(chloromethyl)propyl trifluoromethanesulfonate; 3-chloro-2,2-bis(chloromethyl)propyl trifluoromethylsulfonate; 2,2-bis(chloromethyl)-1,3-propanediyl trifluoromethanesulfonate; 3-bromo-2,2-dimethylpropyl trifluoromethanesulfonate; 2,2-bis(bromomethyl)-n-butyl trifluoromethanesulfonate; 3-bromo-2,2-bis(bromomethyl)propyl trifluoromethanesulfonate; 2,2-bis(bromomethyl)-1,3-propanediyl trifluoromethanesulfonate; triflate esters of brominated dimers, trimers, etc. of polyols such as pentaerythritol, trimethylol ethane, trimethylol propane, neopentyl glycol, etc.; 2,2-bis[(2,4,6-tribromophenoxy)methyl]-1,3propanediyl trifluoromethanesulfonate; 3-bromo-2,2-bis[(2,4,6-tribromophenoxy)methyl]-1-propyl trifluoromethanesulfonate; and the like.

As used herein, "dimers, trimers, etc." refers to ether derivatives of the polyols to which they refer. Such ether derivatives comprise repeating units of polyol residues connected through an ether linkage such as is formed by condensation reaction of one or more hydroxyl groups of one polyol molecule with a hydroxyl group of one or more other polyol molecules. Thus for example, the dimer of 2,2-bis(bromomethyl)-1,3-propanediol (i.e.,

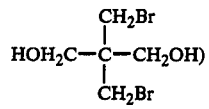

has the formula:

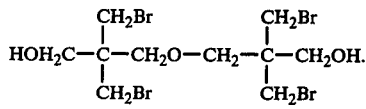

Of particular interest as char-forming agents are the aforementioned triflate esters wherein R is an inertly substituted n-valent tertiary hydrocarbyl radical containing one or more bromine atoms. Preferably the bromine content of the inertly substituted radical is such that the ratio of halogen atoms to carbon atoms in R is from about 1:10 to about 1:1, most preferably from about 1:2 to about 1:1.

Especially preferred as char-forming agents are the triflate esters having the formula:

$$(CF_3-\underset{\underset{O}{\|}}{\overset{\overset{O}{\|}}{S}}-O-CH_2)_{\overline{m}}C-(CH_2R')_{4-m}$$

wherein $m$ is 1 or 2 and each R' group is independently bromine or an inertly substituted aliphatic, alicyclic or aromatic halohydrocarbon radical containing from 1 to about 6 carbon atoms and from 1 to about 4 atoms of bromine. Preferably such R' group is independently bromine or tribromophenoxy.

The triflate esters of the invention can be conveniently prepared by contacting trifluoromethanesulfonic anhydride with a cooled (e.g., 0° C.), stirred solution containing an inert organic solvent such as methylene chloride, an acid acceptor such as pyridine, and a hydroxy-containing compound of the formula:

R-(CH_2OH)_n wherein $n$ and R are as previously defined. The procedure for preparing esters of para-toluenesulfonic acid described by Fieser et al., "Reagents for Organic Synthesis," John Wiley & Sons, Inc., New York, N.Y., 1967, p. 1180 can be conveniently employed in the preparation of such triflate esters.

The appropriate hydroxy-containing compounds of the aforementioned structure to be used for a given triflate ester will be readily apparent to the skilled artisan. Examples of such compounds include neopentyl alcohol; neopentyl glycol; trimethylol ethane; trimethylol propane; pentaerythritol; dimers, trimers, etc. of polyols such as neopentyl glycol, trimethylol ethane, trimethylol propane, and pentaerythritol; 3-bromo-2,2-dimethylpropanol; 2,2-bis(bromomethyl)propanol; 3-bromo-2,2-bis(bromomethyl)propanol; 2,2-bis(bromomethyl)-1,3-propanediol; 3-chloro-2,2-dimethylpropanol; 2,2-bis(chloromethyl)propanol; 3-chloro-2,2-bis(chloromethyl)propanol; 2,2-bis(chloromethyl)-1,3-propanediol; 2-(chloromethyl)-2-ethyl-1,3-propanediol; 2-(bromomethyl)-2-ethyl-1,3-propanediol; 2,2-bis(chloromethyl)-1-butanol; 2,2-bis(bromomethyl)-1-butanol; brominated dimers, trimers, etc. of polyols such as neopentyl glycol, trimethylol ethane, trimethylol propane and pentaerythritol; and similar hydroxy-containing compounds of the aforementioned formula.

The use of the triflate esters of the invention in char-forming polymer compositions is fully described in the disclosure of Ser. No. 688,862, which has hereinbefore been incorporated by reference.

Exemplary triflate esters of the invention have been found to exhibit activity as insecticides in the control and killing of insect species as indicated in Table B.

TABLE B

| INSECTICIDAL ACTIVITY | | |
|---|---|---|
| Trifluoro-methanesulfonate | Concentration (PPM) | Insect Species |
| 3-chloro-2,2-bis(chloromethyl)propyl | 400 | Codling moth |
|  | 400 | Beet army worm larvae |
| 3-bromo-2,2-dimethylpropyl | 400 | Beet army worm larvae |
| 3-bromo-2,2-bis(bromomethyl)propyl | 1.5 to 25 | West spot cucumber beetle larvae |
| 2,2-bis(bromomethyl)-propanediyl | 400 | Cabbage looper |
| 2,2-bis[(2,4,6-tribromophenoxy) methyl]-1,3-propanediyl | 100 to 400 | Two spotted spider mite |

In addition, certain of the triflate esters of the invention have been found to exhibit activity as antimicrobial agents in the control and killing of fungus and bacteria species as indicated in Table C.

TABLE C

| ANTIMICROBIAL ACTIVITY | | |
|---|---|---|
| Trifluro-methanesulfonate | Concentration (PPM) | Microbe Species |
| 3-chloro-2,2-bis-(chloromethyl) propyl 3-bromo-2,2-bis-(bromomethyl) propyl | 400 | Apple mildew |
|  | 500 | Trichophton mentagrophytes |
|  | 100 to 500 | Mycobacterium phlei |
|  | 500 | Bacillus subtilis |
| 2,2-bis(bromomethyl)-propanediyl | 500 | Staphylococcus aureus |
|  | 100 to 500 | Trichophton mentagrophytes |
|  | 100 to 500 | Aspergillus niger |
|  | 100 to 500 | Bacillus subtilis |
|  | 500 | Pullularia pullulans |
|  | 10 to 500 | Mycobacterium phlei |
|  | 100 to 500 | Ceratocystis ips |
|  | 100 to 500 | Trichoderm sp. madison p-42 |
|  | 400 | Fungus-apple scab |

Finally, certain of the triflate esters of the invention have been found to exhibit activity as herbicides in the control and killing of plant species as indicated in Table D.

TABLE D

| HERBICIDAL ACTIVITY | | |
|---|---|---|
| Trifluoro-methanesulfonate | Concentration | Plant Species |
| 3-chloro-2,2-bis(chloromethyl)propyl | 10 lbs/acre | Pig weed |
|  | 10 lbs/acre | Wild oats |
| 2,2-bis(bromomethyl)-1,3-propanediyl | 10 lbs/acre | Barnyard grass |
|  | 10 lbs/acre | Wild oats |
|  | 10 lbs/acre | Velvet leaf |
|  | 4 lbs/100 gal water | White winter wheat |

TABLE D-continued

| HERBICIDAL ACTIVITY | | |
|---|---|---|
| Trifluoro-methanesulfonate | Concentration | Plant Species |
|  | 4 lbs/100 gal water | Corn |
|  | 4 lbs/100 gal water | Sorghum/milo |

Use of the aforementioned active triflate esters in such antimicrobial, herbicidal and insecticidal applications is pursuant to techniques conventionally employed in the art.

The preparation of the triflate esters of the invention and their use in char-forming polymer compositions are illustrated by the following examples.

EXAMPLE 1

Preparation of Additive A:
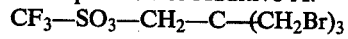

A solution of 25.5 grams (0.09 mole) of trifluoromethanesulfonic anhydride in methylene chloride is added dropwise, with stirring, over a 1½ hour period to a solution containing 26.0 grams (0.08 mole) of 3-bromo-2,2-bis(bromomethyl)-1-propanol and 6.3 grams (0.08 mole) pyridine in 75 ml of methylene chloride, at 0° C.

The reaction product is recovered by:
(1) washing the reaction mixture with 100 ml of cold distilled water in a separatory funnel and draining off the methylene chloride solution layer;
(2) drying the methylene chloride layer over anhydrous sodium sulfate;
(3) filtering out the sodium sulfate; and
(4) vacuum distillation of the methylene chloride.

The product recovered in a colorless liquid exhibiting a boiling point of 102° C. at 0.03 mm of mercury and a nuclear magnetic resonance (NMR) spectrum in agreement with that expected for 3-bromo-2,2-bis(bromomethyl)-propyl trifluoromethanesulfonate. A 33.5-gram portion of the product is recovered, representing a yield of 91.5 percent.

Preparation of Additive B:
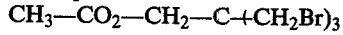

For comparative purposes a quantity of 3-bromo-2,2-bis(bromomethyl)-propyl acetate is prepared by reacting the 3-bromo-2,2-bis(bromomethyl)-1-propanol with acetic acid.

Preparation of Char-forming Compositions

Polystyrene compositions and styrene/maleic anhydride copolymer compositions, comprising 75 mole percent styrene and 25 mole percent maleic anhydride, each containing the aforementioned triflate ester are prepared by blending the ester into the polystyrene, or the styrene/maleic anhydride copolymer, with a Brabender° mixer at 180° or 220° C., respectively. In the same manner, compositions containing the aforementioned acetate and polystyrene, or the styrene/maleic anhydride copolymer, are prepared. The resulting compositions are molded into test bars and subjected to a modified version of the Underwriters Laboratory Vertical Burning Test for Classifying Materials 94V-0, 94V-1, or 94V-2. Such tests demonstrate the ignition properties or burning characteristics of the polymer compositions when exposed to small-scale ignition sources. It should be noted, however, that all known synthetic polymers will burn when subjected to a sufficiently intense heat source. Thus the test results may not reflect the properties of the polymer composition under actual fire conditions. The test procedure and test results are summarized in Table I.

TABLE I

| Sample | Polymer | Additive[1] Type | Additive[1] Wt. % | Wt. % Bromine | Wt. % Halogen | Indicated UL 94 Rating | Avg. Time of Flaming Combustion | Visible Char Formation |
|---|---|---|---|---|---|---|---|---|
| 1* | Styrene/maleic anhydride copolymer (75:25) | None | — | — | — | Sustained Combustion | — | — |
| 2 | " | A | 5 | 2.6 | 3.3 | 94V-2 | 5 sec. | Yes |
| 3* | " | B | 5 | 3.3 | 3.3 | 94V-2 | 11 sec. | No |
| 4 | " | A | 10.3 | 5.4 | 6.7 | 94V-0 | <1 sec. | Yes |
| 5* | " | B | 10.3 | 6.7 | 6.7 | 94V-0 | 6 sec. | No |
| 6 | Polystyrene | A | 10.3 | 5.4 | 6.7 | 94V-2 | 3 sec. | No |
| 7* | " | B | 10.3 | 6.7 | 6.7 | 94V-2 | 10 sec. | No |

*Samples 1,3,5 % and 7 are not embodiments of the invention.
[1]A: 3-bromo-2,2-bis(bromomethyl)-propyl trifluoromethanesulfonate
B: 3-bromo-2,2-bis(bromomethyl)-propyl acetate
[2]Test specimens, 5.0 inches in length by 0.50 inch in width with a maximum thickness of 0.50 inch, are ignited in a draft-free environment while supported vertically lengthwise by a holding clamp attached to the upper ¼ inch of the specimen with the lower end 12 inches above a horizontal layer of dry absorbent surgical cotton having a maximum free-standing thickness of ⅜ inch. Ignition is performed using a Bunsen burner adjusted to produce a ¾ inch blue flame. The flame is placed centrally under the lower end of the test specimen for 10 seconds and is then withdrawn. When flaming of the specimen ceases, the flame is placed immediately under the specimen for 10 more seconds and is again withdrawn. The parameters observed for classification are:
a. Duration of flaming following the first flame application.
b. Duration of flaming following the seconds flame application.
c. Duration of flaming and glowing following the second flame application.
d. Whether or not the specimens burned up to the holding clamp.
e. Whether or not the specimens dripped flaming particles which ignited the surgical cotton.
Results indicative of a 94V-O rating are achieved by meeting the following criteria:
a. None of the specimens burn with flaming combustion for more than 10 seconds after each flame application.
b. The specimens exhibit no more than an average 10 seconds total flaming combustion for the 2 flame applications combined.
c. None of the specimens burn with flaming or glowing combustion up to the holding clamp.
d. None of the specimens drip flaming particles that ignite the cotton below the specimens.
e. None of the specimens exhibit glowing combustion persisting longer than 30 seconds after the second flame removal.
Results indicative of a 94V-2 rating are achieved by meeting the following criteria:
a. None of the specimens burn with flaming combustion for more than 30 seconds after each flame application.
b. The specimens exhibit no more than an average 50 seconds total flaming combustion for the 2 flame applications combined.
c. None of the specimens burn with flaming or glowing combustion to the holding clamp.
d. Only briefly burning flaming drips, some of which ignited the cotton below the specimen are observed.
e. None of the specimens exhibit glowing combustion more than 60 seconds after the second flame removal.

As is apparent from Table I, the samples containing styrene/maleic anhydride copolymer and the triflate esters form char upon combustion while the samples containing styrene/maleic anhydride copolymer and the corresponding acetate ester do not. Neither the acetate ester nor the triflate ester induce char formation in styrene homopolymer.

It should be noted in comparing the results for triflate- and acetate-containing samples at the same additive loadings that such samples have equivalent halogen content by weight and that the acetate-containing samples have a higher bromine content by weight than the triflate-containing samples. It should further be noted that the samples containing triflate esters consistently exhibited significantly shorter average duration of flaming combustion than did the corresponding acetate-containing samples and that this phenomenon was observed both for polystyrene and for styrene/maleic anhydride copolymer as the polymer component.

EXAMPLE 2

Preparation of Additive C:
$(CF_3-SO_3-CH_2)_2C-(CH_2Br)_2$

Pursuant to the procedure for preparing Additive A in Example 1, 200 grams (0.72 mole) of trifluoromethanesulfonic anhydride is reacted with 94.2 grams (0.36 mole) of 2,2-bis(bromomethyl)-1,3-propanediol. The reaction product is recovered by recrystallization from hexane, yielding 137 grams (72 percent yield) of solid product exhibiting a melting point range of 67°-70° C. The NMR spectrum confirms the above identified structure.

Preparation of Additive D:

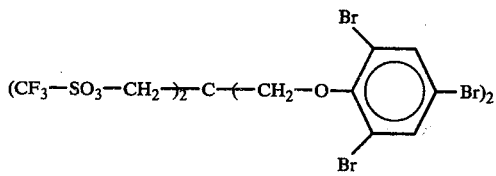

A quantity of 3-bromo-2,2-bis(bromomethyl)-1-propanol is treated with base to form 3,3-bis(bromomethyl)oxetane which is then reacted, with stirring, at room temperature for 30 hours, with a stoichiometric amount of potassium 2,4,6-tribromophenate dissolved in dimethyl formamide. The reaction product formed, 3,3-bis[(2,4,6-tribromophenoxy)methyl]oxetane, is recovered by pouring the reaction mixture into a quantity of distilled water and extracting the resulting mixture twice with methylene chloride. The methylene chloride layers are combined, washed with water, separated from the water wash, and dried over anhydrous sodium sulfate. The sodium sulfate is removed by filtration and the methylene chloride is removed by vacuum distillation on a steam bath. Recrystallization of the resulting crude product from a carbon tetrachloride-hexane mixture provides 3,3-bis[(2,4,6-tribromophenoxy)methyl]oxetane in a 74 percent yield.

The oxetane thus obtained is refluxed for 3 hours in a 15:1 volume ratio mixture of acetic acid and sulfuric acid. The 2,2-bis[(2,4,6-tribromophenoxy)methyl]-1,3-propanediacetate thus formed is recovered by extraction with methylene chloride, which is thereafter removed by vacuum distillation. The resulting diacetate is then refluxed with an excess of methanol in the presence of sodium hydroxide until the NMR spectrum indicates that hydrolysis of the acetate is complete. The resulting product, 2,2-bis[(2,4,6-tribromophenoxy)methyl]-1,3-propanediol, is recovered by (1) removal of the remaining methanol by vacuum distillation, (2) extraction of the product with carbon tetrachloride, (3) drying the CCl$_4$ layer over anhydrous sodium sulfate, and (4) removal of the CCl$_4$ under a vacuum. The 2,2-bis[(2,4,6-tribromophenoxy)methyl]-1,3-propanediol thus recovered is then reacted with trifluoromethanesulfonic anhydride according to the following procedure.

A solution of 29.6 grams (0.105 mole) of trifluoromethanesulfonic anhydride in 50 ml of methylene chloride is added dropwise, with stirring, over a 20-minute period to a slurry of 40 grams (0.053 mole) of 2,2-bis[(2,4,6-tribromophenoxy)methyl]-1,3-propanediol and 8.3 grams (0.105 mole) of pyridine in 200 ml of methylene chloride. The reaction is allowed to proceed overnight with stirring. The product is recovered in the manner described for Additive A in Example 1, and is further purified by recrystallization from a 2:1 volume ratio mixture of carbon tetrachloride and hexane. The solid product recovered has a melting point range of 142°–145° C. Elemental analysis of the solid product confirms that the solid product is 2,2-bis[(2,4,6-tribromophenoxy)methyl]-1,3-propanediyl trifluoromethanesulfonate.

Preparation of Additive E:

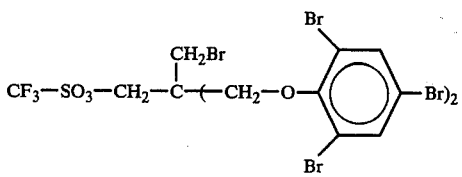

A quantity of 3,3-bis[(2,4,6-tribromophenoxy)methyl]oxetane, produced pursuant to the procedure for Additive D, is reacted in a carbon tetrachloride solution with 62 percent aqueous hydrogen bromide for 30 minutes in a steam bath. The reaction mixture is washed (a) twice with water, (b) once with a dilute sodium bicarbonate solution, and (c) for a third time with water. The carbon tetrachloride layer is separated and dried over anhydrous sodium sulfate. The CCl$_4$ is then removed under a vacuum and the remaining material is further purified by recrystallization of CCl$_4$. The resulting product has a melting point range of 85°–89° C. and an NMR spectrum in agreement with that expected for 3-bromo-2,2-bis[(2,4,6-tribromophenoxy)methyl]-1-propanol.

The 3-bromo-2,2-bis[(2,4,6-tribromophenoxy)methyl]-1-propanol is then reacted with trifluoromethanesulfonic anhydride pursuant to the procedure for Additive A in Example 1. The resulting product is recovered in 68 percent yield and exhibits a melting point range of 151.5°–153° C. Its NMR spectrum corresponds to that expected for 3-bromo-2,2-bis[(2,4,6-tribromophenoxy)methyl]-propyl trifluoromethanesulfonate.

Preparation and Testing of Char-forming Compositions

Styrene/maleic anhydride copolymer (75:25) compositions containing Additives A, C, D or E are prepared by blending in a Brabender ® mixer as in Example 1. In the same manner 75:25 styrene/maleic anhydride copolymer compositions containing 3-bromo-2,2-bis(bromomethyl)-propyl acetate (i.e., Additive B) are prepared for comparison.

The weight loss of the compositions as a function of temperature is determined by thermogravimetric analysis using a duPont 990 Thermal Analyzer in an air atmosphere at a heating rate of 10° C./minute. The difference between the residual weight of sample containing additive and the residual weight of a sample without additive provides a quantitative measure of the effectiveness of such additive as a char formation promoter in 75:25 styrene/maleic anhydride copolymer. The weights remaining at 450° C. for the various compositions and the difference between the residual weights of the samples with and without additive are summarized in Table II.

TABLE II

Thermogravimetric Analysis of 75:25 Styrene/Maleic Anhydride Copolymer Compositions

| Sample | Additive[1] | wt. % Additive | Residue at 450° C (%)[2,3] | Residue with Additive Minus Residue of Control (i.e., Sample 8) (%)[4] |
|---|---|---|---|---|
| 8* | None | — | 12 | 0 |
| 9* | B | 5 | 15 | 3 |
| 10 | A | 5 | 19 | 7 |
| 11 | C | 5 | 26 | 14 |
| 12* | B | 10 | 10 | −2 |
| 13 | A | 10 | 24 | 12 |
| 14 | C | 10 | 24 | 12 |
| 15 | C | 15 | 27 | 15 |
| 16 | D | 15 | 31 | 19 |
| 17 | E | 15 | 28 | 16 |

*Samples 8, 9 and 12 are not embodiments of the invention.
[1] A: 3-bromo-2,2-bis(bromomethyl)-propyl trifluoromethanesulfonate.
B: 3-bromo-2,2-bis(bromomethyl)-propyl acetate.
C: 2,2-bis(bromomethyl)-1,3-propanediyl trifluoromethanesulfonate.
D: 2,2-bis[(2,4,6-tribromophenoxy)methyl]-1,3-propanediyl trifluoromethanesulfonate.
E: 3-bromo-2,2-bis[2,4,6-tribromophenoxy)methyl]-propyl trifluoromethanesulfonate.
[2] The residue % figure represents the weight of the sample remaining at 450° C divided by the original sample weight before exposure to elevated temperatures times 100%. The experimental error in such numbers is approximately ±2%.
[3] All samples exhibited essentially complete weight loss upon continued heating to 650° C.
[4] The additive-containing sample residue at 450° C minus the sample No. 8 residue at 450° C (i.e, 12% ±2%). The experimental error in each of the numbers is approximately ±2%. Thus the resulting error in the calculated difference is approximately ±4%.

The results show that the samples containing triflate esters exhibit significantly more residue at 450° C. (i.e., from about 50 percent to about 150 percent more) than the 75:25 styrene/maleic anhydride copolymer control (Sample 8). The data for Sample Nos. 9, 10, 12 and 13 show that equivalent increases in residue at 450° C. are not obtained when the corresponding acetate ester is substituted for the triflate ester.

While the present invention has been described with reference to particular embodiments and examples, it should be understood that such embodiments are not intended to limit the scope of the instantly claimed invention.

What is claimed is:

1. An ester having the formula:

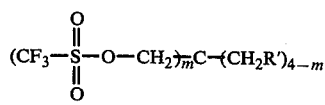

wherein $m$ is 1 or 2 and each R' is independently bromine or a bromophenoxy radical containing from 1 to 4 atoms of bromine.

2. The ester of claim 1 wherein each R' is individually bromine or tribromophenoxy.

3. The ester of claim 2 selected from the group consisting of 3-bromo-2,2-bis(bromomethyl)propyl trifluoromethanesulfonate; 2,2-bis(bromomethyl)-1,3-propanediyl trifluoromethanesulfonate; 3-bromo-2,2-bis[(2,4,6-tribromophenoxy)methyl]-propyl trifluoromethanesulfonate; or 2,2-bis[(2,4,6-tribromophenoxy)methyl]-1,3-propanediyl trifluoromethane sulfonate.

4. The ester of claim 2 wherein $m$ is 2.

5. The ester of claim 4 corresponding to the name 2,2-bis(bromomethyl)-1,3-propanediyl trifluoromethanesulfonate.

6. The ester of claim 4 corresponding to the name 2,2-bis[(2,4,6-tribromophenxoy)methyl]-1,3-propanediyl trifluoromethanesulfonate.

7. The ester of claim 2 corresponding to the name 3-bromo-2,2-bis(bromomethyl)propyl trifluoromethanesulfonate.

8. The ester of claim 2 corresponding to the name 3-bromo-2,2-bis[(2,4,6-tribromophenoxy)methyl]propyl trifluoromethanesulfonate.

* * * * *

UNITED STATES PATENT AND TRADEMARK OFFICE
CERTIFICATE OF CORRECTION

PATENT NO. : 4,125,555            Page 1 of 2
DATED : November 14, 1978
INVENTOR(S) : Charles E. Reineke It is certified that error appears in the above-identified patent and that said Letters Patent are hereby corrected as shown below:

Column 1, line 48, delete "2699-2701" and insert --2699-2705--.

Column 1, line 50, delete "Hansen" and insert --P: Hansen--.

Column 2, line 12, delete "as" and insert --an--.

Column 3, line 57, delete "methyl]-1,3propanediyl" and insert --methyl]-1,3-propanediyl--.

Column 5, line 32, first heading of Table C, delete "Trifluro-" and insert --Trifluoro- --.

Column 6, line 34, delete "in" and insert --is--.

Column 7, line 8, sixth heading of Table I, delete "Indicated UL 94 Rating" and insert --Indicated UL 94 Rating[2]--.

UNITED STATES PATENT AND TRADEMARK OFFICE
CERTIFICATE OF CORRECTION

PATENT NO. : 4,125,555
DATED : November 14, 1978
INVENTOR(S) : Charles E. Reineke It is certified that error appears in the above-identified patent and that said Letters Patent are hereby corrected as shown below:

Column 7, in Table I, in the asterisked footnote, delete "%".

Column 7, in Table I, under footnote 2, in "b." delete "seconds" and insert --second--.

Column 12, line 2, delete "2,2-bis[(2,4,6-tribromophenxoy)methyl]-1,3-propaned-" and insert --2,2-bis[(2,4,6-tribromophenoxy)methyl]-1,3-propaned- --.

Signed and Sealed this

First Day of May 1979

[SEAL]

Attest:

RUTH C. MASON
Attesting Officer

DONALD W. BANNER
Commissioner of Patents and Trademarks